(12) United States Patent
Peffly et al.

(10) Patent No.: US 8,435,501 B2
(45) Date of Patent: May 7, 2013

(54) CONDITIONING SHAMPOO COMPOSITIONS

(75) Inventors: Marjorie Mossman Peffly, Cincinnati, OH (US); Jennifer Elaine Hilvert, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 1864 days.

(21) Appl. No.: 11/036,709

(22) Filed: Jan. 14, 2005

(65) Prior Publication Data

US 2005/0158266 A1    Jul. 21, 2005

Related U.S. Application Data

(60) Provisional application No. 60/537,119, filed on Jan. 16, 2004.

(51) Int. Cl.
*A61Q 5/02* (2006.01)

(52) U.S. Cl.
USPC .................. 424/70.12; 424/70.19; 424/70.31

(58) Field of Classification Search .................. None
See application file for complete search history.

(56) References Cited

U.S. PATENT DOCUMENTS

| 5,037,818 | A | 8/1991 | Sime |
| 5,085,857 | A | 2/1992 | Reid |
| 5,456,863 | A | 10/1995 | Bergmann |
| 5,756,720 | A | 5/1998 | Chowdhary |
| 6,180,117 | B1 | 1/2001 | Berthiaume |
| 6,200,554 | B1 * | 3/2001 | Yeoh et al. ................ 424/70.12 |
| 6,316,541 | B1 | 11/2001 | Gee |
| 6,348,188 | B1 | 2/2002 | Eccleson |
| 6,475,474 | B1 | 11/2002 | Ricca |
| 6,706,258 | B1 | 3/2004 | Gallagher et al. |
| 7,541,320 | B2 * | 6/2009 | Dabkowski et al. ........ 510/122 |
| 2001/0006621 | A1 | 7/2001 | Coupe et al. |
| 2003/0133899 | A1 * | 7/2003 | Fan et al. .................. 424/70.17 |
| 2004/0157754 | A1 | 8/2004 | Geary et al. |

FOREIGN PATENT DOCUMENTS

| CA | 2 075 767 | 7/1999 |
| EP | 0432951 A2 | 6/1991 |
| EP | 0468721 A1 | 1/1992 |
| EP | 0529883 A1 | 3/1993 |
| EP | 0 674 898 B2 | 3/2006 |
| WO | WO-95/09599 A1 | 4/1995 |
| WO | WO-95/17880 A1 | 7/1995 |
| WO | WO-9632919 A1 | 10/1996 |
| WO | WO-98/13011 A1 | 4/1998 |
| WO | WO-99/39683 | 8/1999 |
| WO | WO-99/53889 | 10/1999 |
| WO | WO 99/59530 A1 | 11/1999 |
| WO | WO 02/36095 A2 | 5/2002 |
| WO | WO 03/101410 A1 | 12/2003 |
| WO | WO 03/101418 A1 | 12/2003 |
| WO | WO-03/105793 A2 | 12/2003 |

OTHER PUBLICATIONS

Dow Corning Corporation—Material Safety Data Sheet 2-8194, Microemulsion, Sep. 26, 2012.

* cited by examiner

*Primary Examiner* — Jyothsna Venkat
(74) *Attorney, Agent, or Firm* — Angela K. Haughey

(57) ABSTRACT

Shampoo compositions comprising at least one surfactant; a silicone oil having an internal phase viscosity of less than about 50,000 cst, wherein said silicone oil is present as a preformed microemulsion of particles having an average particle size of less than about 0.15 microns, a cationic deposition polymer; an aqueous carrier and optionally a stabilizing agent provide a substantially clear shampoo composition, which provides superior conditioning to hair and/or skin while also providing excellent storage stability and high optical transparency or translucency.

9 Claims, No Drawings

CONDITIONING SHAMPOO COMPOSITIONS

CROSS REFERENCE TO RELATED APPLICATION

This application claims the benefit of Provisional Application No. 60/537,119 filed Jan. 16, 2004.

FIELD OF THE INVENTION

This invention relates to shampoo compositions, particularly to shampoo compositions which include an anionic surfactant system, a microemulsion of silicone and a cationic cellulose or guar deposition polymer.

BACKGROUND OF THE INVENTION

Shampoo compositions comprising various combinations of detersive surfactant and conditioning agents are known. These products typically comprise an anionic detersive surfactant in combination with a conditioning agent such as silicone, hydrocarbon oil, fatty esters, or combinations thereof. These products have become more popular among consumers as a means of conveniently obtaining hair and skin conditioning and cleansing performance all from a single personal care product.

However, many shampoo compositions do not provide sufficient deposition of conditioning agents onto hair and skin during the cleansing process. Without such deposition, large proportions of conditioning agent are rinsed away during the cleansing process and therefore provide little or no conditioning benefit. Without sufficient deposition of the conditioning agent on the hair and skin, relatively high levels of conditioning agents may be needed in the personal cleansing composition to provide adequate conditioning performance. However, high levels of a conditioning agent can increase raw material costs, reduce lathering, and present product stability concerns.

Obtaining good deposition of a conditioning agent is further complicated by the action of detersive surfactants in the shampoo composition. Detersive surfactants are designed to carry away or remove oil, grease, dirt, and particulate matter from the hair and skin. In doing so, the detersive surfactants can also interfere with deposition of the conditioning agent, and both deposited and non deposited conditioning agent can be removed during rinsing. This further reduces deposition of the conditioning agent onto the hair and skin after rinsing, thus further reducing conditioning performance.

One known method for improving deposition of a conditioning agent involves the use of certain cationic deposition polymers. These polymers may be natural cellulosic or guar polymers that have been modified with cationic substituents. Selecting a polymer with sufficient charge density and molecular weight in combination with an optimized surfactant system results in sufficient deposition of conditioning agents. When the silicone in these higher deposition systems has a high internal phase viscosity some consumers notice performance tradeoffs in terms of reduced shampoo cleaning, conditioner buildup, and a reduction in volume of the hair style. A high internal phase viscosity refers to viscosities greater than 50,000 cst., and especially those greater than 100,000 cst. Reduction in the deposition of the silicone will reduce these negatives, but will also reduce desirable hair conditioning benefits. Thus, a need still exists for improved conditioning performance in shampoo compositions that does not result in buildup leading to reduced volume and dissatisfaction with the cleansing properties of the shampoo.

Additionally, a recently identified unmet consumer need is the ability to deliver sufficient conditioning performance from a shampoo that is optically clear or at least transparent and does not result in a cleaning tradeoff, buildup, or reduced volume of the intended hair style, and is storage stable. Attempts have been made previously to use dispersed droplets of silicone oil deposited on the hair shaft to provide this conditioning. However, these attempts have resulted in either insufficient conditioning, buildup of conditioning agents, reduction of style volume, or product instability in the form of reduced product clarity and/or an unacceptable reduction in shampoo viscosity over time.

It is known in the art that oily cosmetic agents such as silicones can be incorporated into cosmetic compositions by means of microemulsification, whereby the silicone is present as stably emulsified droplets of a particle size of about 0.15 microns or less.

However, by the very nature of the form in which microemulsified particles of a conditioning oil are incorporated into cosmetic compositions, the conditioning benefits attainable are frequently limited, owing to a poor level of deposition on the intended site, ie. the hair or the skin. Even if sufficient deposition is accomplished, it often results in decreased cleansing, product build up and/or decreased volume. Additionally, storage stability issues such as a significant reduction in product clarity and/or viscosity over time are common with this approach.

Additionally, attempts have been made in the art to use higher internal phase viscosity (>50,000 cst) silicones to provide clear conditioning shampoos. The use of these high viscosity materials presents several technical challenges. The main technical challenges are the reduced cleaning, product buildup, and reduced volume described above. Additionally, attempts have been made to use lower internal phase viscosity (15,000 cst) silicones to provide clear conditioning shampoos. In the past, the use of lower viscosity materials had resulted in conditioning performance tradeoffs and/or viscosity stability tradeoffs. The lack of conditioning performance is likely the result of the inappropriate combination of polymer and surfactant system resulting in poor silicone deposition. Additionally, these attempts have resulted in formulations which are very unstable, showing a significant drop in shampoo viscosity over a relatively short period of time.

Accordingly the need remains for a substantially clear shampoo composition, which delivers superior conditioning benefits to hair and/or skin. The need also remains for a substantially clear shampoo composition, which remains stable/substantially clear after prolonged storage.

SUMMARY OF THE INVENTION

The present invention meets the aforementioned needs by providing a shampoo composition, which provides superior conditioning to hair and/or skin while also providing excellent storage stability and optionally high optical transparency or translucency. These benefits can be obtained by combining a low viscosity microemulsified silicone oil with a cationic deposition polymer.

According to the present invention there is provided a shampoo composition comprising:
(a) from about 2% to about 35% by weight of at least one surfactant; (b) from about 0.01% to about 10% by weight of a silicone oil having an internal phase viscosity of less than about 50,000 cst, wherein said silicone oil is present as a preformed microemulsion of particles having an average particle size of less than about 0.15 microns, the emulsion comprising water, surfactant and the particles; wherein the molar equivalent of surfactant in the total shampoo composition is equal to or greater than the molar equivalent of surfactant in the preformed microemulsion; (c) from about 0.01% to about 10% by weight of a cationic deposition polymer selected from the group consisting of cationic cellulose polymers having a molecular weight of at least about 800,000 and cationic guar polymers having a molecular weight of at least about 800,000 and a charge density of at least about 0.1 meq/g; (d) an aqueous carrier; and (e) optionally from about 0% to about 5% of a stabilizing agent.

In one embodiment of the shampoo composition the surfactant is comprised of an anionic surfactant system,
  a. wherein said anionic surfactant system comprises an ethoxylate level in the amount of 1.04 multiplied by the molecular weight divided by 1.0 MM of said cationic cellulose polymer plus 0.75 to 3.25,
  b. wherein said anionic surfactant system comprises a sulfate level in the amount of 0.42 multiplied by the charge density of said cationic cellulose polymer plus 1.1 to 3.6.

In one embodiment of the shampoo composition the stabilizing agent is a nonionic surfactant in addition to any surfactant already present in the preformed emulsion, wherein the nonionic surfactant is selected from the group consisting of nonionic surfactants having an HLB range of from about 9 to about 18 and present from about 0.05% to about 5% of the total shampoo composition.

In one embodiment of the shampoo composition the silicone comprises less than about 1% cyclotetrasiloxane.

In one embodiment of the shampoo composition wherein the shampoo composition, prior to the addition of any colorants and/or pigments has a percent transmittance at 600 nm of at least about 75%.

In one embodiment of the shampoo composition the composition retains at least about 60% of said compositions original viscosity after a period of at least about seven days at a temperature of about 120° C.

DETAILED DESCRIPTION OF THE INVENTION

While the specification concludes with claims, which particularly point out and distinctly claim the invention, it is believed the present invention will be better understood from the following description.

The shampoo compositions of the present invention include at least one detersive surfactant, a silicone oil microemulsion, a cationic deposition polymer and an aqueous carrier. Each of these essential components, as well as preferred or optional components, are described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "charge density", as used herein, refers to the ratio of the number of positive charges on a monomeric unit of which a polymer is comprised to the molecular weight of said monomeric unit. Charge density is typically expressed in miliequivalents per gram. The charge density multiplied by the polymer molecular weight determines the number of positively charged sites on a given polymer chain.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "polymer" as used herein shall include materials whether made by polymerization of one type of monomer or made by two (i.e., copolymers) or more types of monomers.

The term "suitable for application to human hair" as used herein, means that the compositions or components thereof so described are suitable for use in contact with human hair and the scalp and skin without undue toxicity, incompatibility, instability, allergic response, and the like.

The term "substantially clear" as used herein, means that the compositions have a percent transparency of at least about 75% transmittance at 600 nm when measured in the absence of dyes and colorants using any standard UV spectrophotometer.

The term "storage stable" as used herein, means the compositions maintain a level of transparency of at least about 70% transmittance at 600 nm when measured in the absence of dyes and colorants for at least 6 months when stored at one (1) atmosphere of pressure, 50% relative humidity, and 25° C., or to approximate rapid aging for 2 weeks at a temperature of 45° C. The term "storage stable" may also refer to the shampoo viscosity stability wherein the viscosity of the finished shampoo composition drops no more than 40% of the shampoo compositions initial viscosity for at least 6 months when stored at (1) atmosphere of pressure, 50% relative humidity, and 25° C. or to approximate rapid aging for 2 weeks at a temperature of 45° C.

The internal phase viscosity of the silicone being measured is the viscosity of the silicone oil itself and not that of the emulsion or the final shampoo composition. In order to measure the internal phase viscosity of the silicone the emulsion must first be broken to phase separate the silcone oil from the carrier (i.e. water) and surfactants in the microemulsion. Breaking the silicone emulsion is typically accomplished by addition of a sufficient amount of solvent, for example isopropanol, which is not substantially soluble in the silicone, or a stepwise procedure wherein isopropanol addition is followed by acetone addition. After physical separation of the silicone oil from the carrier and surfactants standard viscosity measurement techniques may be used. The preferred viscosity measurement technique involves use of a Brookfield Cone and Plate viscometer and is measured at 25° C.

A. Surfactant

The shampoo compositions of the present invention include an anionic surfactant system. The surfactant component is included to impart cleaning performance to the composition. The surfactant component in turn comprises an ethoxylated surfactant and a sulfate, and optionally a zwitterionic or amphoteric surfactant, an additional surfactant, or a combination thereof. Such surfactants should be physically and chemically compatible with the essential components described herein, or should not otherwise unduly impair product stability, aesthetics or performance.

Suitable anionic surfactant components for use in the shampoo compositions herein include those that are known for use in hair care or other personal care compositions. The concentration of the anionic surfactant component in the shampoo compositions should be sufficient to provide the desired cleaning and lather performance, and generally range from about 2% to about 35%, preferably from about 5% to about 25%, by weight of the shampoo composition.

Preferred anionic surfactants suitable for use in the shampoo compositions are the alkyl sulfates and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from about 1 to about 10, and M is a cation such as ammonium, alkanolamines, such as triethanolamine, monovalent metals, such as sodium and potassium, and polyvalent metal cations, such as magnesium, and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between from about 0 and about 10, preferably from about 2 to about 5, more preferably from about 3, molar proportions of ethylene oxide, and the resulting mixture of molecular species having, for example, an average of 3 moles of ethylene oxide per mole of alcohol, is sulfated and neutralized.

Specific non-limiting examples of alkyl ether sulfates which may be used in the personal care compositions of the present invention include sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0 to 20% by weight $C_{12-13}$ compounds; from 60 to 100% by weight of $C_{14-15-16}$ compounds; from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

A percent ethoxylate can be calculated based on the stochiometry of the surfactant structure, based on a particular molecular weight of the surfactant where the number of moles of ethoxylation is known. Likewise, given a specific molecular weight of a surfactant and a sulfation reaction completion measurement, the percent sulfate can be calculated. Analytical techniques have been developed to measure percent ethoxylation or percent sulfates within surfactant systems. The level of ethoxylate and the level of sulfate representative of a particular surfactant system is calculated from the percent ethoxylation and percent sulfates of individual surfactants in the following manner:

Level of Ethoxylate in a composition=percent ethoxylation multiplied by percent active ethoxylated surfactant.

Level of Sulfate in a composition=percent Sulfate in ethoxylated surfactant multiplied by percent active ethoxylated surfactant plus percent sulfate in non-ethoxylated surfactant multiplied by percent active non-ethoxylated surfactant.

Another suitable class of anionic surfactants are the water-soluble salts of the organic, sulfuric acid reaction products of the general formula $R_1$—$SO_3$-M wherein $R_1$ is chosen from the group consisting of a straight or branched chain, saturated aliphatic hydro-carbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms, and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof.

Additional Surfactants

Suitable amphoteric or zwitterionic surfactants for use in the shampoo compositions herein include those which are known for use in hair care or other personal care compositions. Concentration of such amphoteric surfactants preferably ranges from about 0.5% to about 20%, preferably from about 1% to about 10%, by weight of the composition. Non limiting examples of suitable zwitterionic or amphoteric surfactants are described in U.S. Pat. Nos. 5,104,646, and 5,106,609.

Amphoteric surfactants suitable for use in the shampoo compositions are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Preferred amphoteric surfactants for use in the present invention include cocoamphoacetate, cocoamphodiacetate, lauroamphoacetate, lauroamphodiacetate, and mixtures thereof.

Zwitterionic surfactants suitable for use in the shampoo compositions are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

Optional Surfactants

The shampoo compositions of the present invention may further comprise additional surfactants for use in combination with the surfactant component described hereinbefore. Other suitable anionic surfactants are the water-soluble salts of organic, sulfuric acid reaction products conforming to the formula [R¹—SO₃-M] where R¹ is a straight or branched chain, saturated, aliphatic hydrocarbon radical having from about 8 to about 24, preferably from about 10 to about 18, carbon atoms; and M is a cation described hereinbefore. Non limiting examples of such surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfonates which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the shampoo compositions are the beta-alkyloxy alkane sulfonates. These surfactants conform to the formula:

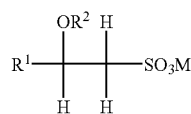

where R¹ is a straight chain alkyl group having from about 6 to about 20 carbon atoms, R² is a lower alkyl group having from about 1 to about 3 carbon atoms, preferably 1 carbon atom, and M is a water-soluble cation as described hereinbefore. Preferred anionic surfactants for use in the personal care compositions include sodium tridecyl benzene sulfonate, sodium dodecyl benzene sulfonate.

Amides, including alkanol amides, are the condensation products of fatty acids with primary and secondary amines or alkanolamines to yield products of the general formula:

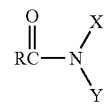

wherein RCO is a fatty acid radical and R is $C_{8-20}$; X is an alkyl, aromatic or alkanol (CHR'CH₂OH wherein R' is H or $C_{1-6}$ alkyl); Y is H, alkyl, alkanol or X. Suitable amides include, but are not limited to cocamide, lauramide, oleamide and stearamide. Suitable alkanolamides include, but are not limited to, cocamide DEA, cocamide MEA, cocamide MIPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA and PPG-2 hydrodroxyethyl coco/isostearyamide. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Suitable optional surfactants include nonionic surfactants. Any such surfactant known in the art for use in hair or personal care products may be used, provided that the optional additional surfactant is also chemically and physically compatible with the essential components of the personal care composition, or does not otherwise unduly impair product performance, aesthetics or stability. The concentration of the optional additional surfactants in the personal care composition may vary with the cleansing or lather performance desired, the optional surfactant selected, the desired product concentration, the presence of other components in the composition, and other factors well known in the art.

Non-limiting examples of other surfactants suitable for use in the personal care compositions are described in McCutcheon's, Emulsifiers and Detergents, 1989 Annual, published by M. C. Publishing Co., and U.S. Pat. Nos. 3,929,678, 2,658, 072; 2,438,091; 2,528,378.

B. Silicone

Preferred silicones for use in the present invention include non-volatile silicones, siloxane gums and resins, aminofunctional silicones, quaternary silicones, and mixtures thereof with each other and with volatile silicones. Examples of suitable silicone polymers for use in the present invention include those disclosed in U.S. Pat. No. 6,316,541.

Silicone oils are flowable silicone materials having a viscosity, as measured at 25° C., of less than about 50,000 centistokes (csk), preferably less than about 30,000 csk, more preferably from about 5 csk to about 50,000 csk, and even more preferably from about 10 csk to about 30,000 csk. Suitable silicone oils for use in the personal care compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used. The silicone oil is present in the composition in an amount of from about 0.1 to about 5% by weight.

Silicone oils include polyalkyl or polyaryl siloxanes which conform to the following formula:

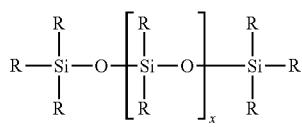

wherein R is aliphatic, preferably alkyl or alkenyl, or aryl, R can be substituted or unsubstituted, and x is an integer from 1 to about 8,000. Suitable substituted R groups for use in the personal care compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Hydroxyl-substituted forms, commonly known as dimethiconols, are the most common silicone found in preformed microemulsions. Examples of dimethiconol microemulsions consistent with the present invention include but are not limited to DC-2-1865 silicone microemulsion, available from Dow Corning. These hydroxyl groups may be further reacted or substituted as desired to further improve performance characteristics or stability of the shampoo composition. Suitable R groups also include timethyl siloxane, cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is described above.

Various methods of making microemulsions of particles of silicones for use in the invention are available and are well known and documented in the art.

One particularly preferred technique for making silicone microemulsions is that described in U.S. Pat. No. 6,316,541 referred to above.

In that document there is described a method of making a stable microemulsion of high molecular weight silicone polymer and water by sequentially adding at an effective rate a standard emulsion comprising polydiorganosiloxane precursor, surfactant and water to a polymerization catalyst medium while mixing to form a clear, stable aqueous microemulsion of polydiorganosiloxane.

The silicone may, for example, be a liquid at ambient temperatures, so as to be of a suitable viscosity to enable the material itself to be readily emulsified to the required particle size of less than about 0.15 microns, the particles of the silicone oil may be less than about 0.1 microns.

The amount of silicone incorporated into the compositions of the invention depends on the type of composition and the material used. A preferred amount is from about 0.01 to about 10% by weight of the shampoo composition, although these limits are not absolute. The lower limit is determined by the minimum level to achieve acceptable conditioning for a target consumer group and the upper limit by the maximum level to avoid making the hair and/or skin unacceptably greasy. The activity of the microemulsion can be adjusted accordingly to achieve the desired amount of silicone or a lower level of the preformed microemulsion may be added to the composition.

The microemulsion of silicone oil may be further stabilized by sodium lauryl sulfate or sodium lauryl ether sulfate with 1-10 moles of ethoxylation. Additional emulsifier, preferably chosen from anionic, cationic, nonionic, amphoteric and zwitterionic surfactants, and mixtures thereof may be present. The amount of emulsifier will typically be in the ratio of 1:1 to 1:7 parts by weight of the silicone, although larger amounts of emulsifier can be used, eg. 5:1 parts by weight of the silicone or more. Use of these emulsifiers may be necessary to maintain clarity of the microemulsion if the microemulsion is diluted prior to addition to the shampoo composition.

The detersive surfactant of the shampoo composition may be the same surfactant as the emulsifier in the preformed microemulsion.

The silicone microemulsion may be further stabilized in the shampoo composition by selection of specific emulsifiers for use during the emulsion polymerization process used to make the silicone microemulsion. A suitable emulsion polymerization process is described by U.S. Pat. No. 6,316,541. A typical emulsifier is TEA dodecyl benzene sulfonate which is formed in the process when triethanolamine (TEA) is used to neutralize the dodecyl benzene sulfonic acid used as the emulsion polymerization catalyst. It has been found that selection of the anionic counterion, typically an amine, and/or selection of the alkyl or alkenyl group in the sulfonic acid catalyst can further improve the stability of the microemulsion in the shampoo composition. In general, more hydrophobic amines than triethanol amine and more hydrophobic alkyl or alkenyl groups than dodecyl are preferred. Specifically, amine neutralizers which have a solubility parameter between about 9.5 and about 13.2 are preferred. Examples of preferred amines include but are not limited to triisopropanol amine, diisopropanol amine, and aminomethyl propanol. This amine selection is not limited to use with neutralization of dodedeycl benzene sulfonic acid, it may be used with the other acid catalysts, for example other aliphatic sulfonic acids or aliphatic sulfuric acids. Other acids such as strong acids without aliphatic groups like hydrochloric acid or sulfuric acid are not as useful in the present invention. Alkyl or alkenyl groups that are more hydrophobic than dodecyl are defined as those having a greater number of carbons than the 12 carbons found in the dodecyl group. Thus, examples of groups, which are more hydrophobic than dodecyl include but is not limited to those with 14 or more carbon atoms, for example, groups which contain 14 carbons (tetradecyl), 16 carbons (hexadecyl), and 18 carbons (octadecyl). A commercially available example of a higher chain length acid is tridecyl benzene sulfonic acid, which is available from Stepan Corporation. The total level of acid emulsion polymerization catalyst present in the reaction medium is from about 0.01 to about 30% by weight of the total silicone. Ionic surfactant catalysts are those catalysts which are neutralized acid catalysts containing alkyl or alkenyl groups as described above and are typically used at the higher end of this range.

C. Cationic Cellulose or Guar Polymer

The compositions of the present invention contain a cationic polymer to aid in deposition of the silicone oil component and enhance conditioning performance. Concentrations of the cationic polymer in the composition typically range from about 0.01% to about 3%, preferably from about 0.05% to about 2.0%, more preferably from about 0.1% to about 1.0%. Suitable cationic polymers will have cationic charge densities of at least about 0.4 meq/gm, preferably at least about 0.0.6 meq/gm, but also preferably less than about 7 meq/gm, more preferably less than about 5 meq/gm, at the pH of intended use of the shampoo composition, which pH will generally range from about pH 3 to about pH 9, preferably between about pH 4 and about pH 8. Herein, "cationic charge density" of a polymer refers to the ratio of the number of positive charges on the polymer to the molecular weight of the polymer. The average molecular weight of such suitable cationic guars and cellulose polymers will generally be at least about 800,000

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Suitable cationic polymers for use in the composition include polysaccharide polymers, such as cationic cellulose derivatives. Suitable cationic polysaccharide polymers include those which conform to the formula:

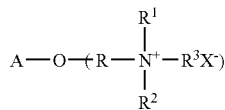

wherein A is an anhydroglucose residual group, such as cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are salts of hydroxyethyl cellulose reacted with trimethyl ammonium substituted epoxide, referred to in the industry (CTFA) as Polyquaternium 10 and available from Amerchol Corporation (Edison, N.J., USA) in their Polymer LR, JR, JP and KG series of polymers. Other suitable types of cationic cellulose includes the polymeric quaternary ammonium salts of hydroxyethyl cellulose reacted with lauryl dimethyl ammonium-substituted epoxide referred to in the industry (CTFA) as Polyquaternium 24. These materials are available from Amerchol Corporation under the tradename Polymer LM-200.

Suitable cationic guar polymers include cationic guar gum derivatives, such as guar hydroxypropyltrimonium chloride, a preferred example of which includes Jaguar Excel commercially available from Rhodia Corporation. Guar polymers consistent with the present invention are described in U.S. Pat. No. 5,756,720.

When used, the cationic polymers herein are either soluble in the composition or are soluble in a complex coacervate phase in the composition formed by the cationic polymer and the anionic, amphoteric and/or zwitterionic detersive surfactant component described hereinbefore. Complex coacervates of the cationic polymer can also be formed with other charged materials in the composition.

Techniques for analysis of formation of complex coacervates are known in the art. For example, microscopic analyses of the compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Preferred cationic polymers include polymers of sufficiently high cationic charge density to effectively enhance deposition efficiency of the solid particle components described herein. Preferred cationic polymers comprise cationic cellulose polymers and cationic guar derivatives with cationic charge densities of at least about 0.5 meq/gm and preferably less than about 7 meq/gm. Preferred cationic cellulose polymers salts of hydroxyethyl cellulose reacted with trimethyl ammonium substituted epoxide, referred to in the industry (CTFA) as Polyquaternium 10 and available from Amerchol Corp. (Edison, N.J., USA) as Ucare Polymer JR30M with a charge density of 1.32 and a molecular weight of approximately 2,000,000, Ucare Polymer KG30M with a charge density of 1.96 and a molecular weight of approximately 2,000,000, and Ucare Polymer JP with a charge density of 0.7 and a molecular weight of approximately 2,000,000.

The above deposition polymers give good clarity and adequate flocculation on dilution with water during use, provided sufficient electrolyte is added to the formulation. Suitable electrolytes include but are not limited to sodium chloride, sodium benzoate, magnesium chloride, and magnesium sulfate.

The deposition polymer is present in an amount of from about 0.01 to about 10% by weight of the total composition, preferably from about 0.01 to about 1% by weight, even more preferably from about 0.04 to about 0.6% by weight.

D. Aqueous Carrier

The cosmetic compositions of the invention are preferably aqueous based, water forming the basis of the continuous phase of the microemulsion. The compositions preferably comprise water in an amount of from about 20 to about 99% by weight of the total composition.

E. Silicone Microemulsion Stabilizing Components

Compositions of the present invention may contain a stabilizing component, which helps to maintain the viscosity of the shampoo base containing the silicone microemulsion. Upon storage, the viscosity of shampoo bases containing silicone microemulsion can drop nearly 50%, to a level below consumer preference. By adding a stabilizing component, the viscosity of the shampoo composition itself is maintained at a consumer preferred viscosity of at least about 1500 cps. Suitable stabilizing components stabilize the microemulsion structure by preventing the migration of a small weight fraction of silicone from the internal phase of the microemulsion into the continuous phase of the shampoo composition. Said stabilizing components include but are not limited to water soluble thickeners, non-ionic surfactants, and polymeric emulsifiers.

A thickener added in addition to the cationic deposition polymer is an example of a stabilizing component. Examples of thickeners include hydroxyl ethyl cellulose derivatives such as Methocel series available from Amerchol Corporation and the Natrosol series available from Aqualon, crosslinked polyacrylates such the Carbopol series available from Noveon, and Gellan Gum available from CP Kelco Corporation.

Nonionic surfactants are typically found in the preformed silicone microemulsion. Addition of more nonionic surfactants to the shampoo can further enhance stability. Preferred non-ionic surfactants have an HLB range of 9-18. These surfactants can be either straight chained or branched typically containing various levels of ethoxylation/propoxylation. The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain derivatized to yield a Hydrophilic-Lipophilic Balance (HLB) of at least 9. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed monomers of the above, such as ethoxylate/propoxylate species, where the total HLB is preferably greater than or equal to 9. Examples of these nonionic surfactants include but are not limited to BRIJ 35, BRIJ 30, Arlasolve 200, Surfonic L22-24, Tween 20, Volpo-20, Pluronic L64, Pluronic P103, Pluronic L35. Polymeric emulsifiers such as Plantaren 2000 from Cognis, Pemulen TR-1 and Pemulen TR-2 from Noveon, and the Arlacel series from Unichema may also be useful in the present invention. These materials if present are included at a concentration of from about 0.1% to about 0.5% by weight of the total composition.

Product Form

The compositions of the invention are preferably rinse-off compositions, i.e., suitable for applying to the hair and/or skin, left thereon for an appropriate period of time and then rinsed off with water.

Compositions in accordance with the present invention are most preferably optically clear. Depending upon the type of shampoo or silicone employed, one or more additional ingredients conventionally incorporated into shampoo formulations may be included in the compositions of the invention. Such additional ingredients include antibacterial agents, antidandruff agents, foam boosters, perfumes, coloring agents, preservatives, viscosity modifiers, proteins, polymers, buffering or pH adjusting agents, moisturizing agents, herb or other plant extracts and other natural ingredients.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The following examples are presented to further illustrate, but not to limit, the present invention:

| Ingredient | Examples 1-6 | | | | | |
|---|---|---|---|---|---|---|
| | 1 | 2 | 3 | 4 | 5 | 6 |
| Water | q.s. | q.s. | q.s. | q.s. | q.s. | q.s. |
| Polyquaterium 10 [1] | 0.5 | | | 0.5 | | |
| Polyquaterium 10 [2] | | 0.25 | | | | |
| Guar Hydroxypropyl Trimonium Chloride [3] | | | | | 0.1 | 0.2 |
| Polyquaterium 10 [4] | | | 0.1 | | | |
| Sodium Laureth Sulfate (SLE3S - 29% active) [5] | 41.38 | 51.72 | 41.38 | 41.38 | 24.12 | 27.58 |
| Sodium Lauryl Sulfate (SLS - 29% active) [6] | 10.34 | 17.24 | 6.9 | 6.9 | 24.12 | 22.07 |
| Dimethiconol Microemulsion A [7] | 4.0 | | 1.0 | | 4.0 | |
| Low D4 Dimethiconol Microemulsion B [8] | | | | 8.0 | | 8.0 |
| Dimethiconol Microemulsion C [9] | | 1.0 | | | | |
| Disodium Coco Amphodiacetate [10] | 5.0 | | 5.0 | | | |
| Cocoamdopropyl Betaine [11] | | | 2.0 | 6.67 | 6.67 | 6.67 |
| PPG-2 Hydroxyethyl Coco/Isostearamide [12] | 2.0 | 2.0 | 2.0 | 2.0 | 2.0 | 2 |
| Magnesium Chloride, hexahydrate [13] | 0.5 | | | 0.5 | | |
| Sodium Chloride [14] | 0.5 | 0.75 | 1.0 | 0.5 | 1.0 | 1.0 |
| Fragrance | 0.55 | 0.55 | 0.55 | 0.5 | 0.5 | 0.5 |
| Preservatives, pH adjusters | Up to 1% | Up to 1% | Up to 1% | Up to 1% | Up to 1% | Up to 1% |

[1] UCare Polymer JR30M, MW = 2.0 MM, charge density = 1.32 meq./gram, supplier Dow Chemicals
[2] UCare Polymer KG30M, MW = 2.0 MM, charge density = 1.96 meq./gram, supplier Dow Chemicals
[3] Jaguar Excel, supplier: Rhodia.
[4] UCare Polymer JP with MW = 2.0 MM and charge density = 0.7
[5] Sodium Laureth Sulfate at 29% active with an average of approximately 3 moles of ethoxylation, supplier: P&G
[6] Sodium Lauryl Sulfate at 29% active, supplier: P&G
[7] Dow Corning 2-1865; Internal Phase Viscosity = 44,000 cps; 30 nm particle size dimethiconol using TEA dodecyl benzene sulfonate and laureth 23 as primary surfactants, 25% active silicone
[8] Dow Corning 2-1865; Internal Phase Viscosity = 34,000 cps; 30 nm particle size dimethiconol using TEA dodecyl benzene sulfonate and laureth 23 as primary surfactants, 25% active.
[9] Dow Corning 2-1865; Internal Phase Viscosity = 25,400 cps; 30 nm particle size dimethiconol using TEA dodecyl benzene sulfonate and laureth 23 as primary surfactants, 25% active silicone.
[10] Miranol C2M Conc NP, 40% active, supplier: Rhodia.
[11] Tegobetaine F-B, 30% active, supplier: Goldschmidt Chemicals
[12] Promidium 2, supplier Unichema
[13] Magnesium Chloride 6-Hexahydrate, supplier Fisher Chemicals
[14] Sodium Chloride USP (food grade), supplier Morton.

The following are representative of shampoo compositions of the present invention providing enhanced stability:

| Ingredient | 7 | 8 | 9 | 10 | 11 |
|---|---|---|---|---|---|
| Water | q.s. | q.s. | q.s. | q.s. | q.s. |
| Polyquaterium 10 [1] | 0.5 | | | 0.5 | |
| Polyquaterium 10 [2] | | 0.25 | | | |
| Guar Hydroxypropyl Trimonium Chloride [3] | | | | | 0.2 |
| Cationic Cellulose Polymer [4] | | | 0.1 | | |
| Gellan Gum [5] | | | | .25 | |

-continued

| Ingredient | 7 | 8 | 9 | 10 | 11 |
|---|---|---|---|---|---|
| Sodium Laureth Sulfate (SLE3S - 29% active) [6] | 41.38 | 51.72 | 41.38 | 41.38 | 27.58 |
| Sodium Lauryl Sulfate (SLS - 29% active) [7] | 10.34 | 17.24 | 6.9 | 6.9 | 22.07 |
| Dimethiconol Microemulsion A [8] | | | 1.0 | | |
| Dimethiconol Microemulsion B [9] | | | | | 8.0 |
| Low D4 Dimethiconol Microemulsion D [10] | | 1.0 | | 8.0 | |
| Dimethiconol Microemulsion with Alternate Amine Neutralizer E [11] | 4.0 | | | | |
| Disodium Coco Amphodiacetate [12] | 5.0 | | 5.0 | | |
| Laureth 23 [13] | | | | | 0.2 |
| Cocoamdopropyl Betaine [14] | | | | 6.67 | 6.67 |
| PPG-2 Hydroxyethyl Coco/Isostearamide [15] | 2.0 | 2.0 | 2.0 | 2.0 | 2 |
| Magnesium Chloride, hexahydrate [16] | 0.5 | | | 0.5 | |
| Sodium Chloride [17] | 0.5 | 0.75 | 0.25 | 0.5 | 1.0 |
| Fragrance | 0.55 | 0.55 | 0.55 | 0.5 | 0.5 |
| Preservatives, pH adjusters | Up to 1% | Up to 1% | Up to 1% | Up to 1% | Up to 1% |

[1] UCare Polymer JR30M, MW = 2.0 MM, charge density = 1.32 meq./gram, supplier Dow Chemicals
[2] UCare Polymer KG30M, MW = 2.0 MM, charge density = 1.96 meq./gram, supplier Dow Chemicals
[3] Jaguar Excel, supplier: Rhodia.
[4] Experimental Polyquaterium 10 polymer with MW = 2.0 MM and charge density = 0.7 meq./grams, supplier Dow Chemicals
[5] Gellan Gum, supplier CP Kelco.
[6] Sodium Laureth Sulfate at 29% active with an average of approximately 3 moles of ethoxylation, supplier: P&G
[7] Sodium Lauryl Sulfate at 29% active, supplier: P&G
[8] Dow Corning 2-1865; Internal Phase Viscosity = 44,000 cps; 30 nm particle size dimethiconol using TEA dodecyl benzene sulfonate and laureth 23 as primary surfactants, 25% active silicone
[9] Dow Corning 2-1865; Internal Phase Viscosity = 34,000 cps; 30 nm particle size dimethiconol using TEA dodecyl benzene sulfonate and laureth 23 as primary surfactants, 25% active.
[10] Experimental microemulsion Internal Phase Viscosity = 25,400 cps; 30 nm particle size dimethiconol, <1% D4 achieved through a Dow Corning Steam Stripping process, 25% active silicone, supplier: Dow Corning
[11] Dow Corning Experimental samples, Internal Phase Viscosity = 25,000,; 30 nm particles size dimethiconol, using TIPA dodecyl benzene sulfonate and laureth 23 as the primary surfactants, 25% active silicone.
[12] Miranol C2M Conc NP, 40% active, supplier: Rhodia.
[13] Tegobetaine F-B, 30% active, supplier: Goldschmidt Chemicals
[14] Promidium 2, supplier Unichema
[15] Magnesium Chloride 6-Hexahydrate, supplier Fisher Chemicals
[16] Sodium Chloride USP (food grade), supplier Morton.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A shampoo composition consisting of:
   (a) from about 2% to about 35% by weight of at least one surfactant; wherein the surfactant is selected from the group consisting of anionic, cationic, amphoteric, or nonionic surfactants, or mixtures thereof,
   (b) from about 0.01% to about 10% by weight of a silicone oil having an internal phase viscosity of from about 5 csk about 50,000 csk, wherein said silicone oil is present as a preformed microemulsion of particles having an average particle size of less than about 0.15 microns, the emulsion comprising:
   (i) water,
   (ii) surfactants selected from the group consisting of TEA dodecyl benzene sulfonates, laureth 23 and combinations thereof and
   (iii) the silicone oil;
   wherein the molar equivalent of surfactant in the shampoo composition is equal to or greater than the molar equivalent of surfactant in the preformed microemulsion;
   (c) from about 0.01% to about 10% by weight of a cationic deposition polymer selected from the group consisting of cationic cellulose polymers having a molecular weight of at least about 800,000 and cationic guar polymers having a molecular weight of at least about 800,000 and a charge density of at least about 0.1 meq/g;
   (d) an aqueous carrier; and
   (e) from about 0.1% to about 0.5% of a stabilizing agent.

2. A shampoo composition according to claim 1 wherein the particles of silicone oil have a particle size of less than about 0.1 microns.

3. A shampoo composition according to claim 1 wherein the silicone oil is present in the shampoo composition in an amount of from about 0.1 to about 5% by weight.

4. A shampoo composition according to claim 1 wherein the cationic deposition polymer is a cationic cellulose polymer.

5. A shampoo composition according to claim 1 wherein the cationic deposition polymer is Polyquaterium 10.

6. A shampoo composition according to claim 1 wherein the cationic deposition polymer is a cationic guar polymer.

7. A shampoo composition according to claim 6 wherein the cationic guar polymer is guar hydroxypropyl trimonium chloride.

8. A shampoo composition according to claim 1 wherein the stabilizing agent is a polymeric water soluble thickener.

9. A shampoo composition according to claim 1 wherein the stabilizing agent is a nonionic surfactant in addition to any surfactant already present in the preformed emulsion, wherein the nonionic surfactant is having an HLB range of from about 9 to about 18.

* * * * *